United States Patent
Grobbee et al.

(10) Patent No.: US 9,867,684 B2
(45) Date of Patent: Jan. 16, 2018

(54) SYSTEM AND PROCESS FOR MANUFACTURING OF DENTURES

(71) Applicant: Global Dental Science, LLC, Scottsdale, AZ (US)

(72) Inventors: Johannes Petrus Michael Grobbee, Oosterbeek (NL); Scott C. Keating, Louisville, CO (US)

(73) Assignee: Global Dental Sciences LLC, Scottsdale, AZ (US)

( * ) Notice: Subject to any disclaimer, the term of this patent is extended or adjusted under 35 U.S.C. 154(b) by 0 days.

(21) Appl. No.: 13/830,963

(22) Filed: Mar. 14, 2013

(65) Prior Publication Data

US 2014/0272796 A1    Sep. 18, 2014

(51) Int. Cl.
| | |
|---|---|
| *A61C 13/00* | (2006.01) |
| *A61C 13/093* | (2006.01) |
| *A61C 13/01* | (2006.01) |
| *A61C 13/08* | (2006.01) |

(52) U.S. Cl.
CPC ...... *A61C 13/1006* (2013.01); *A61C 13/0004* (2013.01); *A61C 13/01* (2013.01); *A61C 13/08* (2013.01)

(58) Field of Classification Search
CPC .. A61K 6/0026; A61C 13/08; A61C 13/1006; A61C 13/0004; A61C 13/01
USPC ................................. 433/171, 199.1
See application file for complete search history.

(56) References Cited

U.S. PATENT DOCUMENTS

| | | | | |
|---|---|---|---|---|
| 200,445 | A * | 2/1878 | Fahnestock et al. | 433/199.1 |
| 321,847 | A * | 7/1885 | Peirce et al. | 433/199.1 |
| 711,324 | A * | 10/1902 | Lacy | 433/173 |
| 1,223,450 | A * | 4/1917 | Van Allen | 433/199.1 |
| 1,293,627 | A * | 2/1919 | Bowers | 433/199.1 |
| 1,585,348 | A * | 5/1926 | Hick et al. | 264/18 |
| 1,652,910 | A | 12/1927 | Psayla | |
| 1,714,185 | A * | 5/1929 | Morgan | 433/188 |
| 1,863,591 | A * | 6/1932 | Crowell | 106/38.3 |
| 1,914,606 | A * | 6/1933 | Kinna et al. | 433/184 |
| 2,107,181 | A * | 2/1938 | Guyton | 433/199.1 |
| 2,418,833 | A * | 4/1947 | Harris | A61C 13/24 |
| | | | | 433/199.1 |
| 2,472,492 | A * | 6/1949 | Saffir | 156/61 |

(Continued)

FOREIGN PATENT DOCUMENTS

| | | |
|---|---|---|
| CA | 2505892 | 5/2004 |
| JP | 2008307281 | 12/2008 |

(Continued)

OTHER PUBLICATIONS

PCT; International Search Report and Written Opinion dated Jul. 18, 2012 in Application No. PCT/US2011/059230.

(Continued)

*Primary Examiner* — Cris L Rodriguez
*Assistant Examiner* — Mirayda A Aponte
(74) *Attorney, Agent, or Firm* — Harvey Law; Derrick Harvey

(57) ABSTRACT

A layered denture having at least one of an integrated layer, balanced occlusion, and a root approximating structure is disclosed. The resulting denture may be suitable for use without an underlying reinforcement bar and may provide enhanced aesthetics by approximating natural dentition and roots both above and below the gum line.

6 Claims, 16 Drawing Sheets

(56) References Cited

U.S. PATENT DOCUMENTS

| | | | |
|---|---|---|---|
| 2,641,835 A * | 6/1953 | Greenmun | 433/199.1 |
| 2,985,961 A * | 5/1961 | Schwartz | 433/213 |
| 2,994,957 A | 8/1961 | Mcleod | |
| 3,083,459 A * | 4/1963 | McMurry et al. | 433/171 |
| 3,241,238 A | 3/1966 | Kertsten | |
| 3,644,996 A * | 2/1972 | Weinkle | 433/171 |
| 3,667,123 A * | 6/1972 | Huey | 433/171 |
| 3,727,309 A * | 4/1973 | Huey | 433/171 |
| 3,748,739 A | 7/1973 | Thibert | |
| 3,813,777 A * | 6/1974 | Van Handel et al. | 433/171 |
| 3,844,702 A | 10/1974 | Dimmer et al. | |
| 4,029,632 A * | 6/1977 | Gross et al. | 524/442 |
| 4,227,877 A | 10/1980 | Tureaud et al. | |
| 4,247,287 A * | 1/1981 | Gigante | 433/199.1 |
| 4,299,573 A | 11/1981 | Ricci | |
| 4,533,325 A * | 8/1985 | Blair et al. | 433/171 |
| 4,591,341 A * | 5/1986 | Andrews | 433/6 |
| 4,634,377 A | 1/1987 | Behrend | |
| 4,784,608 A | 11/1988 | Mays | |
| 4,931,016 A | 6/1990 | Sillard | |
| 5,098,296 A | 3/1992 | Cullen | |
| 5,151,044 A | 9/1992 | Rotsaert | |
| 5,188,529 A | 2/1993 | Luth | |
| 5,340,309 A * | 8/1994 | Robertson | A61C 19/045 433/215 |
| 5,427,906 A | 6/1995 | Hansen | |
| 5,672,305 A | 7/1997 | Kogure | |
| 5,711,668 A | 1/1998 | Huestis | |
| 5,716,214 A | 2/1998 | Lund | |
| 5,718,584 A * | 2/1998 | Wong | 433/168.1 |
| 5,833,461 A | 11/1998 | Wong | |
| 5,839,900 A | 11/1998 | Billet et al. | |
| 6,056,547 A | 5/2000 | Names | |
| 6,139,322 A * | 10/2000 | Liu | 433/199.1 |
| 6,149,427 A | 11/2000 | Van Handel | |
| 6,224,372 B1 | 5/2001 | Ibsen et al. | |
| 6,227,851 B1 * | 5/2001 | Chishti et al. | 433/24 |
| 6,384,107 B2 * | 5/2002 | Liu | 523/118 |
| 6,422,864 B1 | 7/2002 | Glatt | |
| 6,488,503 B1 | 12/2002 | Lichkus et al. | |
| 6,616,444 B2 | 9/2003 | Andreiko et al. | |
| 6,851,949 B1 | 2/2005 | Sachdeva | |
| 7,021,934 B2 | 4/2006 | Aravena | |
| 7,153,135 B1 * | 12/2006 | Thomas | 433/213 |
| 7,234,940 B2 | 6/2007 | Weissman | |
| 7,433,810 B2 | 10/2008 | Pavloskaia et al. | |
| 7,474,932 B2 | 1/2009 | Geng | |
| 7,758,345 B1 * | 7/2010 | Christensen | 433/214 |
| 8,043,091 B2 * | 10/2011 | Schmitt | 433/196 |
| 8,348,669 B1 | 1/2013 | Schmitt | |
| 8,567,408 B2 * | 10/2013 | Roettger et al. | 128/861 |
| 8,641,938 B2 | 2/2014 | Howe | |
| 8,801,431 B2 | 8/2014 | Thompson | |
| 9,055,993 B2 | 6/2015 | Grobbee et al. | |
| 2002/0015934 A1 | 2/2002 | Rubbert et al. | |
| 2002/0180760 A1 | 12/2002 | Rubbert et al. | |
| 2003/0108845 A1 | 6/2003 | Giovannone | |
| 2003/0162147 A1 * | 8/2003 | Dequeker | 433/167 |
| 2003/0163291 A1 | 8/2003 | Jordan et al. | |
| 2003/0211444 A1 | 11/2003 | Andrews | |
| 2004/0005530 A1 | 1/2004 | Mullaly | |
| 2004/0029068 A1 | 2/2004 | Sachdeva et al. | |
| 2004/0219490 A1 | 11/2004 | Gartner et al. | |
| 2005/0175957 A1 | 8/2005 | Haje | |
| 2005/0186539 A1 | 8/2005 | McLean et al. | |
| 2005/0284489 A1 | 12/2005 | Ambis | |
| 2006/0040232 A1 | 2/2006 | Shoup | |
| 2006/0040236 A1 | 2/2006 | Schmitt | |
| 2006/0063135 A1 | 3/2006 | Mehl | |
| 2006/0210945 A1 | 9/2006 | Savic et al. | |
| 2006/0286507 A1 * | 12/2006 | Dequeker | A61C 13/1013 433/167 |
| 2007/0154868 A1 | 6/2007 | Scharlack et al. | |
| 2007/0231774 A1 | 10/2007 | Massad | |
| 2008/0085489 A1 | 4/2008 | Schmitt | |
| 2008/0090207 A1 * | 4/2008 | Rubbert | 433/171 |
| 2008/0127698 A1 | 6/2008 | Luckey et al. | |
| 2008/0206710 A1 | 8/2008 | Kruth et al. | |
| 2008/0206714 A1 | 8/2008 | Schmitt | |
| 2008/0209974 A1 | 9/2008 | Ewolski et al. | |
| 2008/0300716 A1 | 12/2008 | Kopelman | |
| 2009/0148813 A1 | 6/2009 | Sun et al. | |
| 2009/0162813 A1 | 6/2009 | Glor | |
| 2009/0287332 A1 | 11/2009 | Adusumilli et al. | |
| 2009/0291407 A1 | 11/2009 | Kuo | |
| 2009/0325125 A1 | 12/2009 | Diangelo et al. | |
| 2010/0015572 A1 * | 1/2010 | Dierkes et al. | 433/199.1 |
| 2010/0062394 A1 | 3/2010 | Jones et al. | |
| 2010/0086186 A1 | 4/2010 | Zug et al. | |
| 2010/0094446 A1 | 4/2010 | Baloch et al. | |
| 2010/0105011 A1 | 4/2010 | Karkar et al. | |
| 2010/0324875 A1 | 12/2010 | Kalili | |
| 2011/0045442 A1 | 2/2011 | Adusumilli | |
| 2011/0112804 A1 | 5/2011 | Chishti et al. | |
| 2011/0129796 A1 | 6/2011 | Riggio | |
| 2011/0236856 A1 * | 9/2011 | Kanazawa | A61C 13/1003 433/199.1 |
| 2011/0244417 A1 | 10/2011 | Hilsen et al. | |
| 2012/0058449 A1 | 3/2012 | Sklarski et al. | |
| 2012/0095732 A1 | 4/2012 | Fisker et al. | |
| 2012/0100500 A1 | 4/2012 | Gao | |
| 2012/0178045 A1 * | 7/2012 | Massad | 433/171 |
| 2012/0179281 A1 | 7/2012 | Steingart et al. | |
| 2012/0258426 A1 * | 10/2012 | Boe | A61C 13/1006 433/171 |
| 2012/0285019 A1 | 11/2012 | Schechner et al. | |
| 2012/0329008 A1 | 12/2012 | Fishman et al. | |
| 2013/0108988 A1 | 5/2013 | Simoncic | |
| 2013/0209962 A1 * | 8/2013 | Thompson | A61C 13/0004 433/191 |
| 2013/0216978 A1 | 8/2013 | Thompson et al. | |
| 2013/0218532 A1 | 8/2013 | Thompson et al. | |
| 2013/0221554 A1 | 8/2013 | Jung et al. | |
| 2013/0249132 A1 | 9/2013 | Thompson | |
| 2013/0280672 A1 | 10/2013 | Thompson | |
| 2013/0316302 A1 * | 11/2013 | Fisker | 433/171 |
| 2014/0045967 A1 * | 2/2014 | Thomas et al. | 523/115 |
| 2014/0242539 A1 * | 8/2014 | Fisker | G06F 17/50 433/54 |
| 2014/0272796 A1 | 9/2014 | Grobbee et al. | |
| 2015/0037760 A1 | 2/2015 | Thompson et al. | |
| 2015/0064653 A1 | 3/2015 | Grobbee et al. | |
| 2015/0134094 A1 | 5/2015 | Thompson et al. | |
| 2015/0230891 A1 | 8/2015 | Grobbee et al. | |
| 2015/0245891 A1 | 9/2015 | Grobbee | |
| 2015/0245892 A1 | 9/2015 | Grobbee | |

FOREIGN PATENT DOCUMENTS

| | | |
|---|---|---|
| WO | 2001032096 | 12/2001 |
| WO | 2009105661 | 8/2009 |
| WO | 2009105700 | 8/2009 |
| WO | 2010022479 | 3/2010 |
| WO | 2012041329 | 4/2012 |
| WO | 2012061652 | 5/2012 |
| WO | 2012061655 | 5/2012 |
| WO | 2012061659 | 5/2012 |
| WO | 2012061660 | 5/2012 |
| WO | 2014130536 | 8/2014 |
| WO | 2015031062 | 3/2015 |

OTHER PUBLICATIONS

PCT; International Preliminary Report on Patentability dated May 8, 2013 in Application No. PCT/US2011/059230.

PCT; International Search Report and Written Opinion dated Jul. 18, 2012 in Application No. PCT/US2011/059235.

PCT; International Preliminary Report on Patentability dated May 8, 2013 in Application No. PCT/US2011/059235.

PCT; International Search Report and Written Opinion dated Jul. 9, 2012 in Application No. PCT/US2011/059239.

(56) References Cited

OTHER PUBLICATIONS

PCT; International Preliminary Report on Patentability dated May 8, 2013 in Application No. PCT/US2011/059239.
PCT; International Search Report and Written Opinion dated Jul. 18, 2012 in Application No. PCT/US2011/059240.
PCT; International Preliminary Report on Patentability dated May 8, 2013 in Application No. PCT/US2011/059240.
USPTO; Notice of Allowance dated Jun. 6, 2014 in U.S. Appl. No. 13/249,210.
USPTO; Non-Final Office Action dated Jun. 6, 2014 in U.S. Appl. No. 13/823,466.
USPTO; Restriction Requirement dated Jul. 2, 2014 in U.S. Appl. No. 14/195,348.
EPO; European Search Report and Opinion dated Mar. 3, 2014 in Application No. 11838843.8.
PCT; International Search Report and Written Opinion dated Jul. 25, 2014 in Application No. PCT/US2014/017136.
USPTO; Restriction Requirement dated Sep. 5, 2014 in U.S. Appl. No. 13/823,621.
PCT; International Search Report and Written Opinion dated Aug. 7, 2014 in Application No. PCT/US2014/023654.
USPTO; Non-Final Office Action dated Oct. 23, 2014 in U.S. Appl. No. 13/823,621.
USPTO; Final Office Action dated Nov. 7, 2014 in U.S. Appl. No. 13/830,963.
U.S. Appl. No. 14/768,742, filed Aug. 18, 2013, Removable System and Method for Dentures and Surgical Guides.
U.S. Appl. No. 12/939,138, filed Nov. 3, 2010, Systems and Process for Forming Anatomical Features in Dentures.
U.S. Appl. No. 14/798,717, filed Jul. 14, 2015, Systems and Process for Forming Anatomical Features in Dentures.
U.S. Appl. No. 12/939,141, filed Nov. 3, 2010, System and Process for Optimization of Dentures.
U.S. Appl. No. 13/369,238, filed Feb. 8, 2012, Process and Syystems for Molding Thermosetting Plastics.
U.S. Appl. No. 14/013,295, filed Aug. 29, 2013, Improved Denture Reference and Registration System, now U.S. Appl. No. 9,055,993, Jun. 16, 2015, Grobbee et al.
U.S. Appl. No. 13/830,963, filed Apr. 28, 2015, Denture Reference and Registration System.
U.S. Appl. No. 14/821,097, filed Aug. 7, 2015, System and Method for Manufacturing Layered Dentures.
USPTO; Office Action dated Aug. 21, 2014 in U.S. Appl. No. 14/195,348.
USPTO; Final Office Action dated Oct. 21, 2014 in U.S. Appl. No. 14/195,348.
U.S. Appl. No. 13/823,466, filed Mar. 14, 2013, System and Process for Duplication of Dentures.
U.S. Appl. No. 13/823,621, filed Mar. 14, 2013, Systems and Process for Forming Anatomical Features in Dentures.
U.S. Appl. No. 13/823,662, filed Mar. 14, 2013, System and Process for Optimization of Dentures.
U.S. Appl. No. 13/249,210, filed Sep. 29, 2011, Combination Tool for Anatomical Measurement for Denture Manufacture.
U.S. Appl. No. 13/369,238, filed Feb. 8, 2012, Process and Systems for Molding Thermosetting Plastics.
U.S. Appl. No. 14/013,295, filed Aug. 29, 2013, Improved Denture Reference and Registration System.
U.S. Appl. No. 14/195,348, filed Mar. 3, 2014, System and Method for Manufacturing Layered Dentures.
USPTO; Office Action dated Sep. 24, 2013 in U.S. Appl. No. 13/249,210.
U.S. Appl. No. 12/939,136, filed Nov. 3, 2010, System and Process for Duplication of Dentures.
U.S. Appl. No. 13/249,210, filed Sep. 29, 2011, Combination Tool for Anatomical Measurement for Denture Manufacture, now U.S. Pat. No. 8,801,431, Aug. 12, 2014, Thompson.
U.S. Appl. No. 14/506,338, filed Oct. 3, 2014, System and Method for Manufacturing Layered Dentures.
USPTO; Final Office Action dated Mar. 6, 2014 in U.S. Appl. No. 13/249,210.
USPTO; Restriction Requirement dated Dec. 23, 2013 in U.S. Appl. No. 13/823,466.
EPO; European Search Report dated Mar. 4, 2014 in Application No. 11838839.6.
USPTO; Office Action dated Jan. 5, 2015 in U.S. Appl. No. 12/939,136.
USPTO; Non-Final Office Action dated Apr. 9, 2015 in U.S. Appl. No. 12/939,138.
USPTO; Restriction Requirement dated Feb. 12, 2015 in U.S. Appl. No. 13/369,238.
USPTO; Final Office Action dated Mar. 26, 2015 in U.S. Appl. No. 13/823,466.
USPTO; Non-Final Office Action dated Dec. 19, 2014 in U.S. Appl. No. 14/013,295.
USPTO; Notice of Allowance dated Apr. 13, 2015 in U.S. Appl. No. 14/013,295.
USPTO; Final Office Action dated Sep. 25, 2015 in U.S. Appl. No. 12/939,136.
USPTO; Final Office Action dated Aug. 19, 2015 in U.S. Appl. No. 12/939,138.
USPTO; Non-Final Office Action dated Sep. 21, 2015 in U.S. Appl. No. 13/369,238.
USPTO; Notice of Allowance dated Aug. 24, 2015 in U.S. Appl. No. 13/823,662.
USPTO; Non-Final Office Action dated Aug. 13, 2015 in U.S. Appl. No. 13/830,963.
USPTO; Non-Final Office Action dated Aug. 11, 2015 in U.S. Appl. No. 14/195,348.

\* cited by examiner

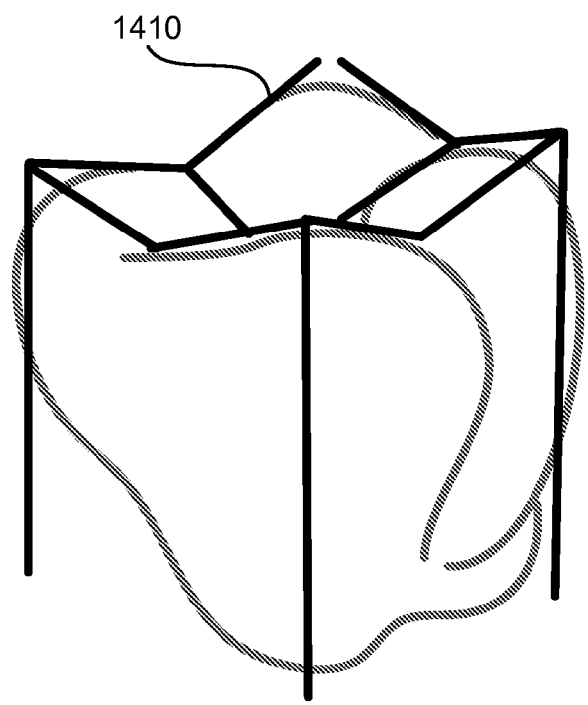
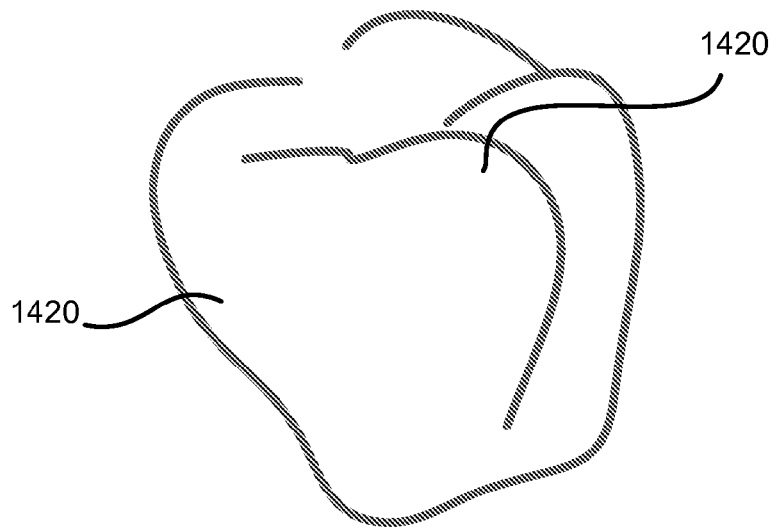
FIG.14

SYSTEM AND PROCESS FOR MANUFACTURING OF DENTURES

FIELD OF INVENTION

The present invention relates to the field of manufacturing dentures. More particularly, the present invention relates to manufacturing of dentures having multiple material layers.

BACKGROUND OF THE INVENTION

Dentures have been manufactured for centuries to replace all or part of an individual's dentition. Dentures have been manufactured by molding the denture from casts made of the patient's edentulous or partially edentulous ridges. The manufacturing process may begin with a preliminary impression of the patient's mouth, which is usually done in silicone or alginate. This impression may be used to prepare a diagnostic cast. While making the impression, the dentist applies pressure to the soft tissues to simulate biting force and extends the borders of the mold to adjacent toothless areas to allow the dentures to better adapt to the gums. A final cast may then be formed from gypsum based on the diagnostic cast. The final cast may be filled or "waxed up" to form the denture. The denture teeth will be set in the wax. The cast with the waxed denture will be placed in a mold and injected or packed with acrylic. Once the resin has cured, the cast may be broken apart and the denture may be removed.

More recently, dentures have been manufactured by machining a void in a block of denture base material formed to match the contour of natural teeth as arranged on a maxilla or on a mandible; filling the void with a synthetic tooth material; removing a portion of the synthetic tooth material; and potentially filling the void and removing a portion of material a second time in order to create denture having teeth made of one or potentially two or more layers.

While machining has been used to form the basic shapes of dentures and denture teeth, prior innovations fail to adequately address the aesthetics and function of the denture, particularly the aesthetics at and below the gum line. For example, in a traditional denture the denture teeth mimic the appearance of a natural tooth only above the gum line because traditional denture teeth adhere to a denture baseplate rather than extending into the baseplate with roots, as would real teeth. Traditional denture teeth are made in standard shapes using injection molding or pressure molding techniques. Anatomical roots are not incorporated in these teeth because of manufacturing difficulties. Currently, a dental technician may festoon root structures in the denture base and use different coloring techniques to paint the dental base to simulate the roots. This requires additional cost, delay, and expense and does not aesthetically mimic a natural tooth as completely as an anatomical root would. Thus there is a need for a denture having a more natural structure that will exhibit an improved aesthetic appearance.

Prior innovations also fail to adequately address the function of traditional dentures with traditional denture teeth. Dentures need to be balanced to avoid the patient's denture becoming loose or unstable during the protrusive and lateral movement of the mandible. This often requires grinding the occlusal surface of the denture teeth until the dentures remain in contact on at least three points throughout much of the movement of the mandible. Traditionally, a denture technician will set up the denture in an articulator and grind the teeth until the occlusive design of the denture is balanced. However, grinding the teeth will take away the enamel layer of the teeth, diminishing the aesthetic appearance of the teeth and functionally weakening the teeth. Thus there is a also need for a denture which is balanced, yet with unground occlusal surface (enamel) so that the denture has a more natural structure that will exhibit an improved aesthetic appearance and will not suffer from weakening of the enamel due to grinding.

Furthermore, in many dentures, a metal bar often sits beneath the denture base to enhance stability and strength. Often if the denture is implant supported, the denture is installed without the bar structure until such time as the patient has healed from the surgery enough so that the inflammation or swelling of the patient's soft tissue has receded to allow the bar structure to fit beneath the denture base. Then a modified denture must be reinstalled, with the bar structure. Furthermore, denture acrylics are often not strong enough to sustain bite forces, thus the base is often mounted on a bar to distribute the forces. This bar can be undesirable due to the associated bulk, cost, weight, and production delay and expense. Thus there is yet another need for a denture having a reinforcement structure but without the bulk, cost, weight, production delay and expense associated with the bar structure.

Accordingly, there remains a need for a denture that more closely simulates natural mouth structures, providing both structural and aesthetical improvements and which, in the case of implant-supported dentures, does not require a follow up procedure to insert a separate bar beneath the denture.

SUMMARY OF THE INVENTION

In accordance with various aspects of the present invention, an improved layered denture is provided. In accordance with an exemplary embodiment, a layered denture comprises a base comprising a first material having a first pocket and a second pocket; an artificial dentition structure in said first pocket wherein said first pocket is configured to support said artificial dentition structure; a reinforcement material wherein said reinforcement material may be filled into a second pocket and machined to provide a support layer; and a second material wherein said second material may be filled into said second pocket and machined to form a covering layer.

In accordance with an exemplary embodiment, a layered denture may be manufactured by iteratively adding layers to cavities or pockets in the denture base and then removing portions of the layers to create portions of the teeth, roots of teeth, reinforcement structures, or other features of the denture. Different layers can be formed from different materials having different strengths, colors, translucency and other material properties. Furthermore, a layered denture may be manufactured according to electronic models, such as three-dimensional digital images, wherein the design of the dentition is adjusted to achieve balanced occlusion.

In accordance with an exemplary embodiment, the material removing operations can be performed in accordance with three-dimensional digital images to create realistic dentures. The three-dimensional digital images can be created from the patient using combinations of digital scanning and bite impressions.

In accordance with an exemplary embodiment, a layered denture may be configured to approximate roots of teeth. The base may have pockets configured to simulate roots when filled with a material. For example a material may be filled in a pocket resulting in a root approximating structure so that the denture has a more realistic appearance.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and:

FIG. 14 illustrates various exemplary artificial dentition structures;

DESCRIPTION OF THE EXAMPLE EMBODIMENTS

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the appended claims.

For the sake of brevity, conventional techniques for manufacturing and construction may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical method of construction.

Figure 1:
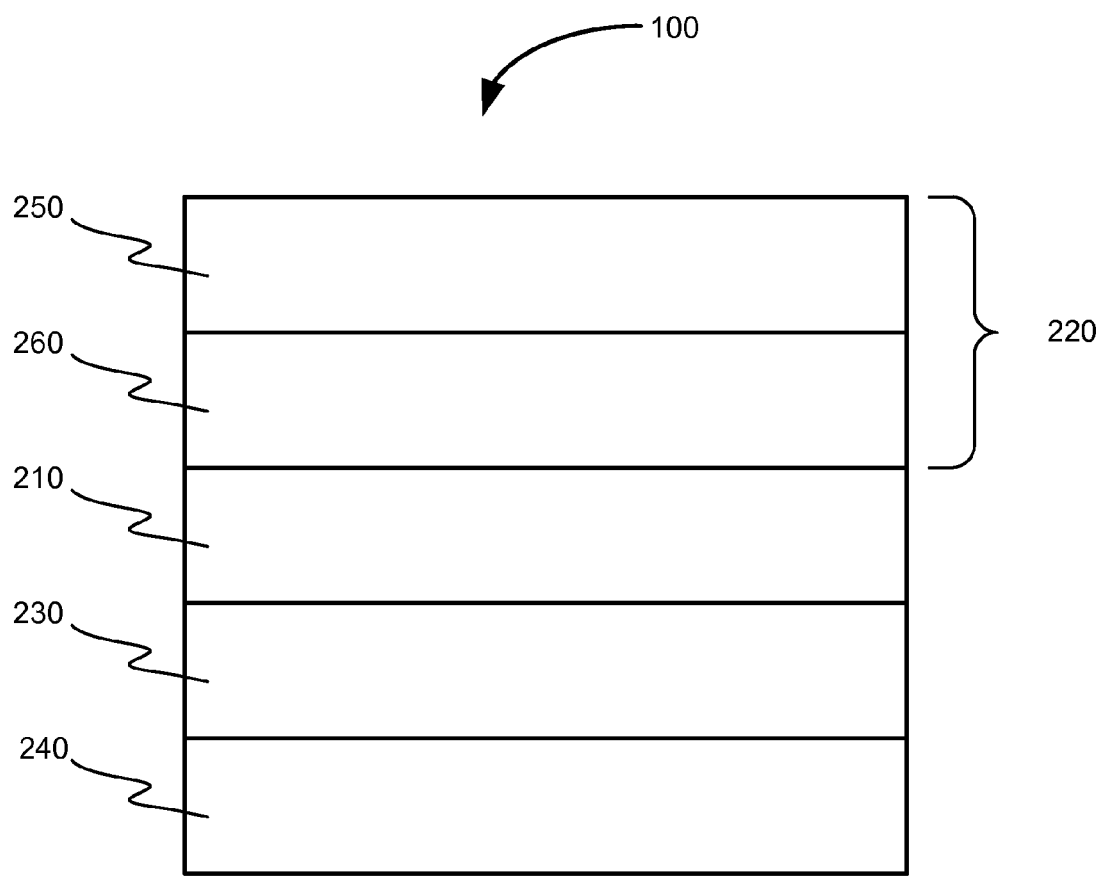
FIG. 1 is a section view of an example embodiment of a layered denture.
Figure 2:
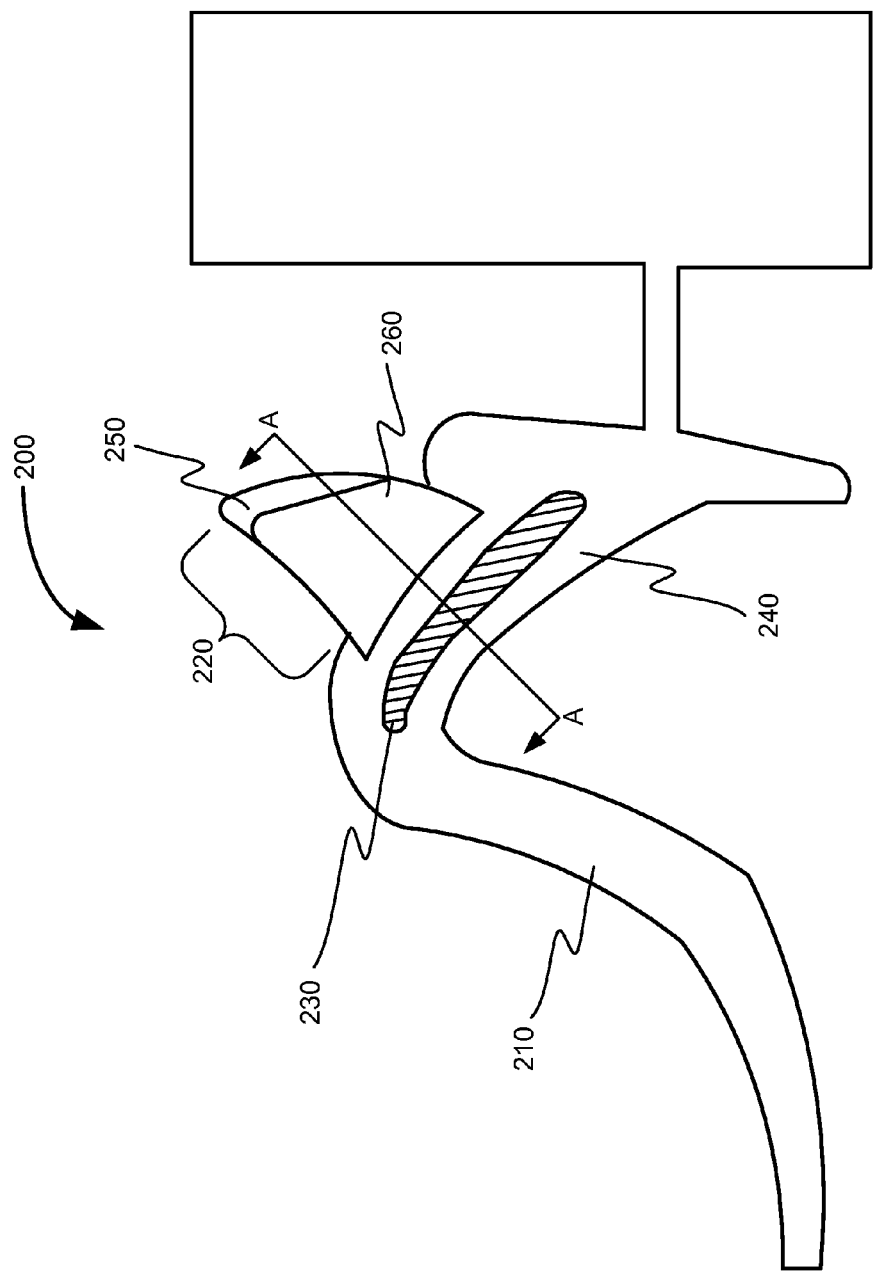
FIG. 2 is a side view of an example embodiment of a layered denture.
Figure 3:
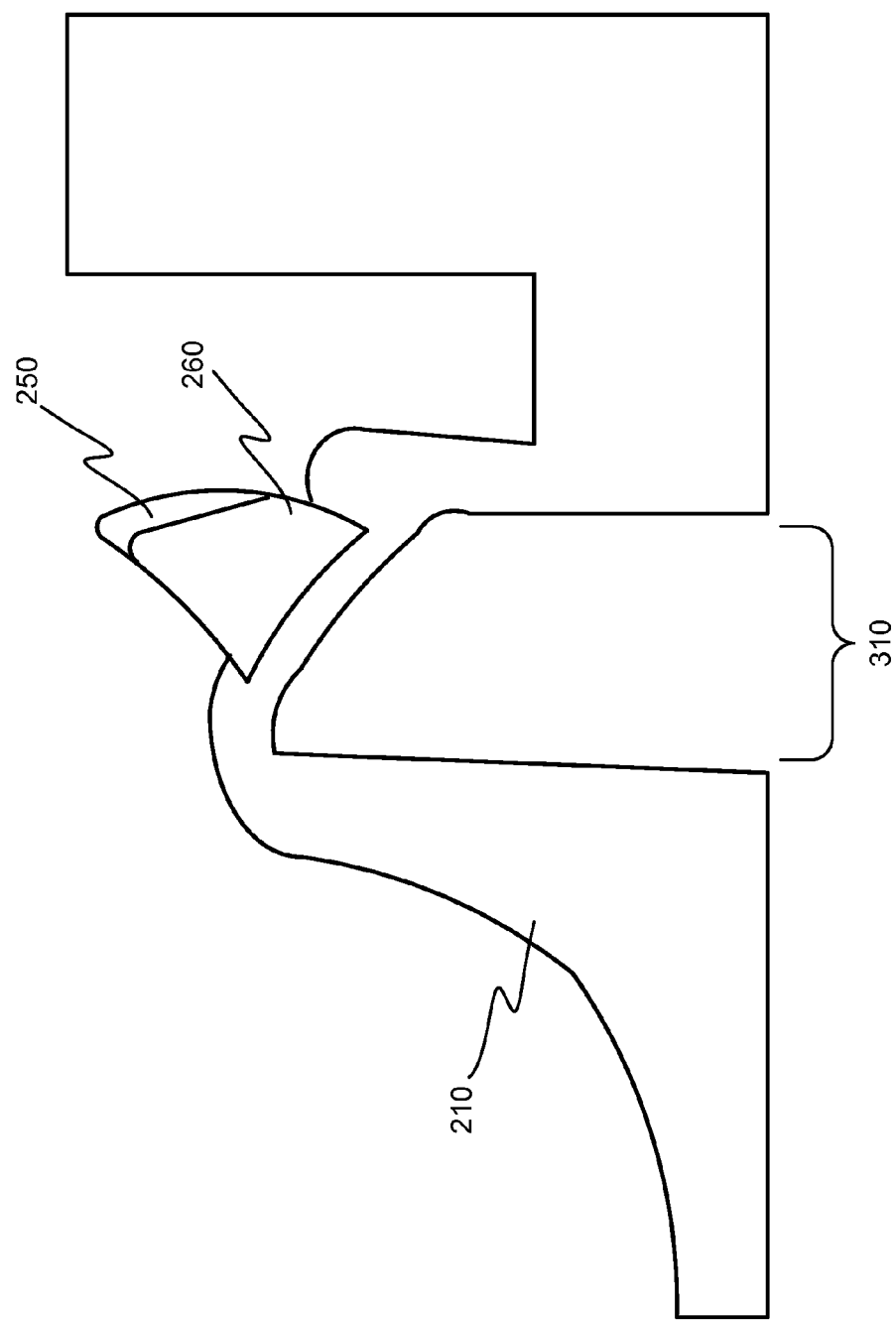
FIG. 3 is a side view of an exemplary layered denture having a second cavity.
Figure 4:
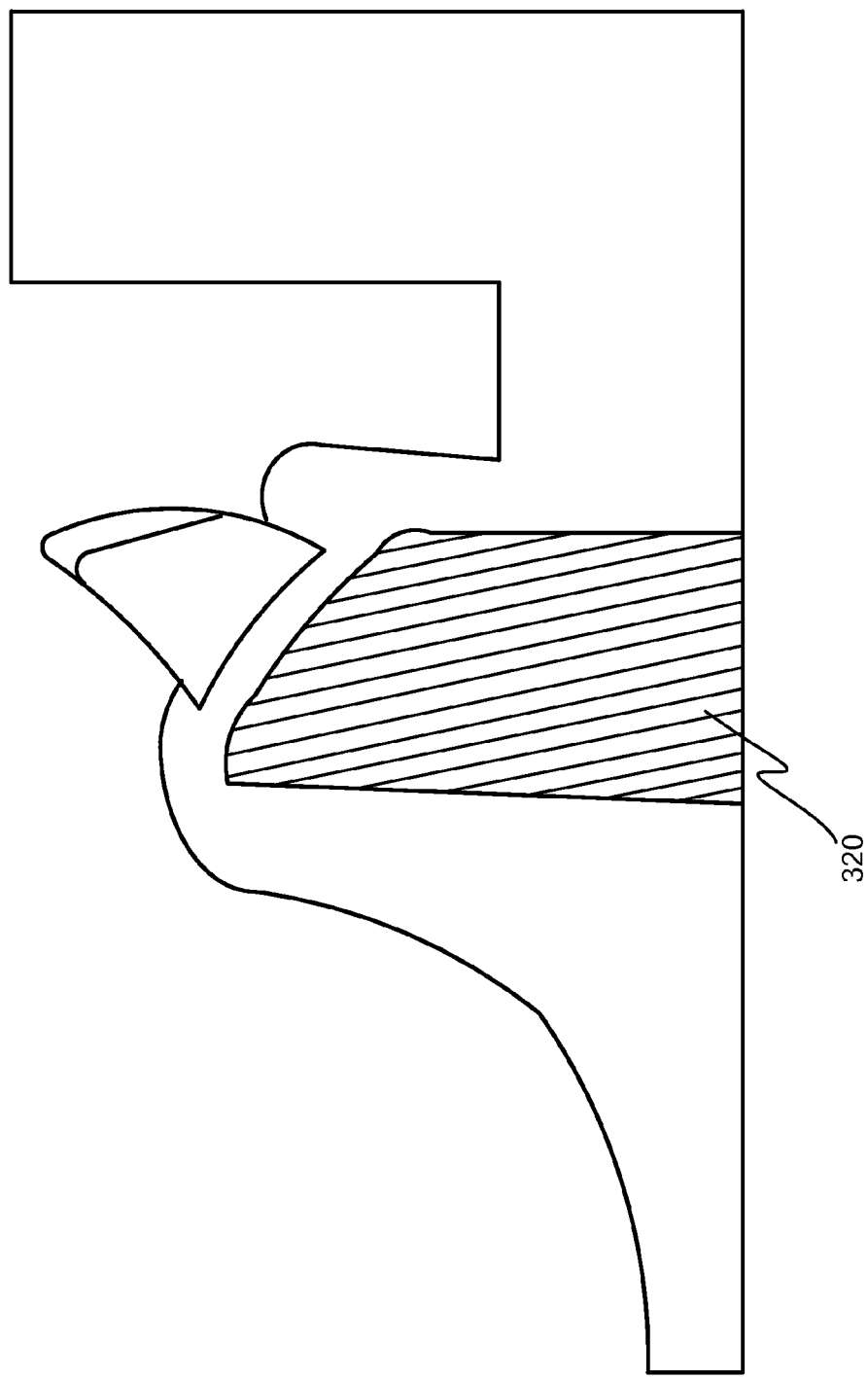
FIG. 4 is a side view of an exemplary layered denture having a second cavity with a second material disposed therein.
Figure 5:
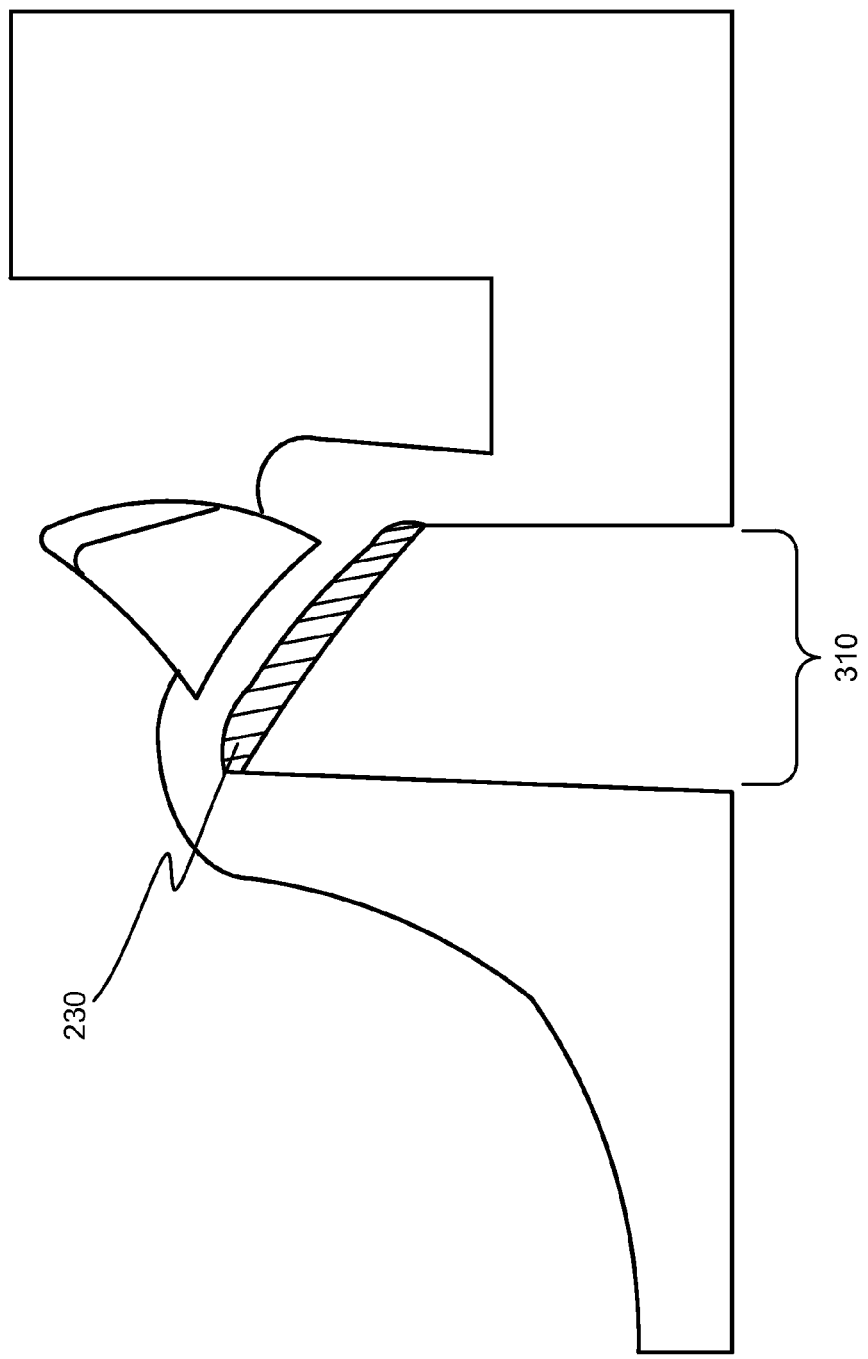
FIG. 5 is a side view of an exemplary layered denture having a second cavity with a support layer disposed therein.
Figure 6:
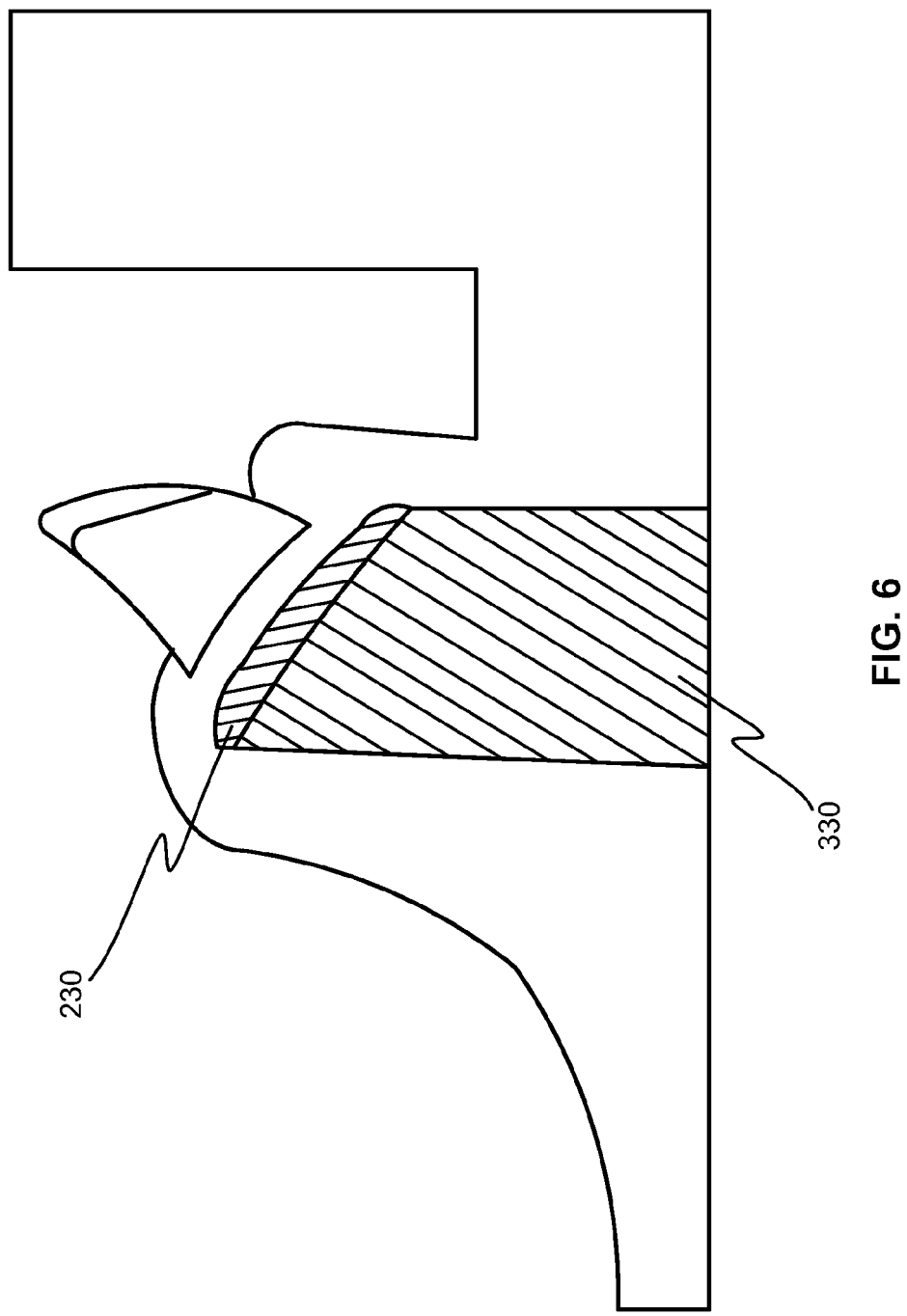
FIG. 6 is a side view of an exemplary layered denture having a covering layer.

Now, with reference to FIGS. 1 and 2, a section view 100 along line A-A is provided of one example embodiment of a layered denture 200 comprising a base 210 comprising a first material having a first pocket and a second pocket; an artificial dentition structure 220 in said first pocket wherein said first pocket is configured to support said artificial dentition structure; a reinforcement material wherein said reinforcement material may be filled into a second pocket and machined to provide a support layer 230 defined by prismatic geometry, e.g., a 3 dimensional structure, (for example, see ¶0035) and oriented parallel to a tangent line of a cross-sectional plane of a mandibular or maxillary ridge and/or oriented perpendicular to a long axis of an artificial dentition structure 220 (e.g., section line A-A shown in FIG. 2), and disposed inward of the artificial dentition structure 220 (for example, see ¶0031; FIGS. 1, 2, 6, 9, and 10), the support layer 230 further comprising a closed boundary coextensive with the artificial dentition structure 220 (for example, see FIGS. 1, 2, 6, 9, and 10) and surrounded by a labial surface and a buccal surface and at least one of a palate of a maxillary ridge and a lingual surface of a mandibular ridge (for example, see FIGS. 1, 2, 6, 9, 10, and 12); and a second material wherein said second material may be filled into said second pocket in a remaining cavity realized after machining of said support layer, said second material further machined to form a covering layer 240. In one example embodiment said covering material is substantially identical to said first material and said covering material integrates into base 210 to form a unitary structure enveloping support layer 230 (for example, see FIG. 2).

In one example embodiment, said base 210 comprises a hardened polymethyl methacrylate (PMMA) material. However, said base may comprise any material having sufficiently low porosity so as to be hygienic for extended placement in a wearer's mouth. For example, said base may be made of a plastic, ceramic, metal, or acrylic, including for instance, a polymer, monomer, composite, or alloy.

Furthermore, said base and any other components of a layered denture 200 may be formed according to a process and system for molding or forming products from thermosetting plastics. Such a system may utilize a deformable container that is placed within the cavity of a housing of a mold with resins and initiator mixed therein. As a piston slides into the cavity, the upper edges of the container may engage between the housing and the piston to seal the housing from leakage. The pressure of the piston along with heat on the housing may enable the curing process to be controlled to maximize compression and minimize porosity. Exemplary processes and systems disclosed in U.S. patent application Ser. No. 13/369,238, PROCESSES AND SYSTEMS FOR MOLDING THERMOSETTING PLASTICS are incorporated by reference.

Furthermore, said base 210 comprising a first material may have a first pocket and a second pocket. Said first pocket and said second pocket may be machined by a CAD/CAM machining device, although any process suited for accurate forming of the material maybe utilized. For example, said first pocket and said second pocket may be formed by machining, etching, waterjet, laser cutting, 3D printing, or chemical mask processes.

In one example embodiment, a layered denture 200 may have an artificial dentition structure 220. In one example embodiment, this structure may be at least one tooth. Said tooth may be constructed according to the principles described herein wherein a first tooth dentition material is filled into the first pocket of base 210 and machined to form a dentin layer 260 and a second tooth dentition material is filled into said first pocket of base 210 and machined to provide an enamel layer 250. The dentin layer 260 may comprise acrylic though any suitable material may be used. The enamel layer 250 may comprise high impact acrylic though any material adapted to be wear and abrasion resistant may be used. In some example embodiments, the dentin layer 260 and/or the enamel layer 250 comprise materials processed by exemplary processes and systems disclosed in U.S. patent application Ser. No. 13/369,238, PROCESSES AND SYSTEMS FOR MOLDING THERMOSETTING PLASTICS, which are incorporated by reference. In some example embodiments these exemplary processes and system enhance the durability of the acrylic or other materials comprising the dentin layer 260 and/or enamel layer 250. In some example embodiments, said artificial dentition structure 220 is electronically defined to achieve balanced occlusion, in accordance with the principles disclosed herein. For example, at least one layer of said artificial dentition structure may be offset to accommodate an enamel layer.

Now, with reference to FIG. 2, in one embodiment of a layered denture 200, covering layer 240 and base 210 are machined to conform to the geometry of a wearer's natural dentition.

As discussed in the background, a metal reinforcement bar may be used to provide reinforcement support to a denture; however, in accordance with the principles disclosed herein, a layered denture 200 may instead comprise a support layer 230 to provide reinforcement support to a layered denture. Said support layer 230 may comprise carbon fiber, though it may alternatively comprise numerous other materials configured to provide support, such as, for example, a Kevlar-brand material, Dynema-brand material, Aramid-brand material, alloy, glass, binder, epoxy, polyester, acrylic, or any material or combination of materials having a desired strength, stiffness, or flexibility sufficient to reinforce said denture. In still other embodiments, layered denture 200 may comprise a plurality of support layers.

In some embodiments, support layer 230 may lie generally parallel to the mandibular or maxillary plane. In other embodiments, support layer 230 may lie generally normal to the mandibular or maxillary ridge, or at any angle with respect to the mandibular ridge or the maxillary ridge. Furthermore, support layer 230 may be non-continuous along the denture. Some embodiments may combine features of various exemplary embodiments.

In some embodiments, a support layer 230 may comprise multiple materials, or any material configuration suitable to enhance or reinforce the resiliency and/or support of the layered denture when subjected to wear in a wearer's mouth or to satisfy other desired chemical, physical, or biological properties. Furthermore, a support layer may comprise materials with differing grain structures or grain direction or with similar grain structures or grain direction or any grain structure or direction suitable for achieving desired properties in the layered denture 200; for example, resiliency under torsional loads. In some embodiments, a support layer 230 may be comprised of carbon, a Kevlar-brand material, Dynema-brand material, Aramid-brand material, alloy, glass, binder, epoxy, polyester, acrylic, or any material or combination of materials suitable for achieving desired properties in the layered denture 200.

A support layer 230 may also be made of materials with differing or similar visual and aesthetic features, such as color, translucency, or gloss, or any visual or aesthetic feature to simulate natural dentition of the patient.

In some example embodiments, the materials comprising a support layer may be self cured, heat-cured, radiation-cured, or illumination-cured, or otherwise rendered solid by any other method. In some example embodiments, the materials comprising a support layer may be cured in accordance with exemplary processes and systems disclosed in U.S. patent application Ser. No. 13/369,238, PROCESSES AND SYSTEMS FOR MOLDING THERMOSETTING PLASTICS are incorporated by reference.

Now, with reference to FIGS. 3-6, a layered denture may be manufactured by a process for manufacturing a layered denture 200 comprising machining a base 210 wherein said machining forms a second pocket 310 in said base, filling a second material 330 into said second pocket 310 into a remaining cavity realized after machining of said support layer 230, said second material further machined to form a covering layer (See FIG. 2; 240). However, in exemplary embodiments wherein support layer includes a reinforcement material 320 comprising a layer fabric or other similar construction, the process of machining said reinforcement material can be eliminated.

Figure 11:
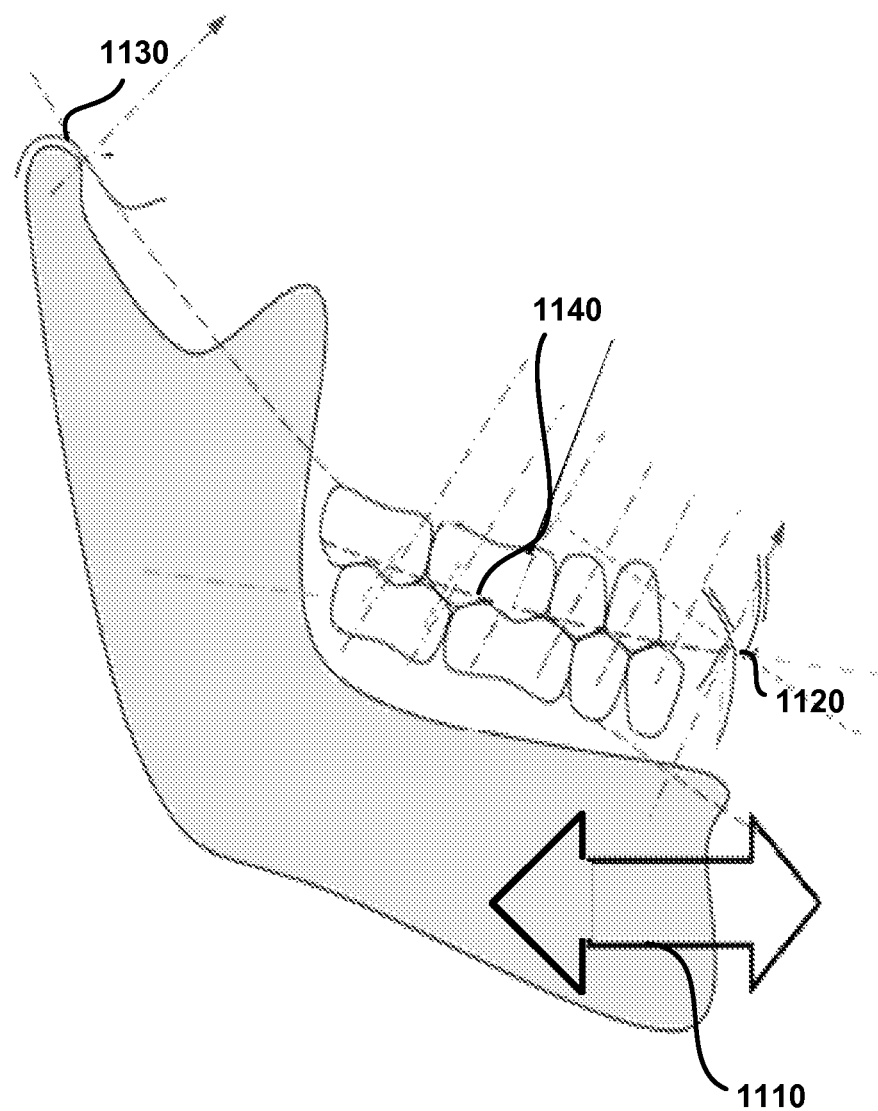
FIG. 11 illustrates an exemplary balanced occlusion motion envelope defined in protrusion.
Figure 12:
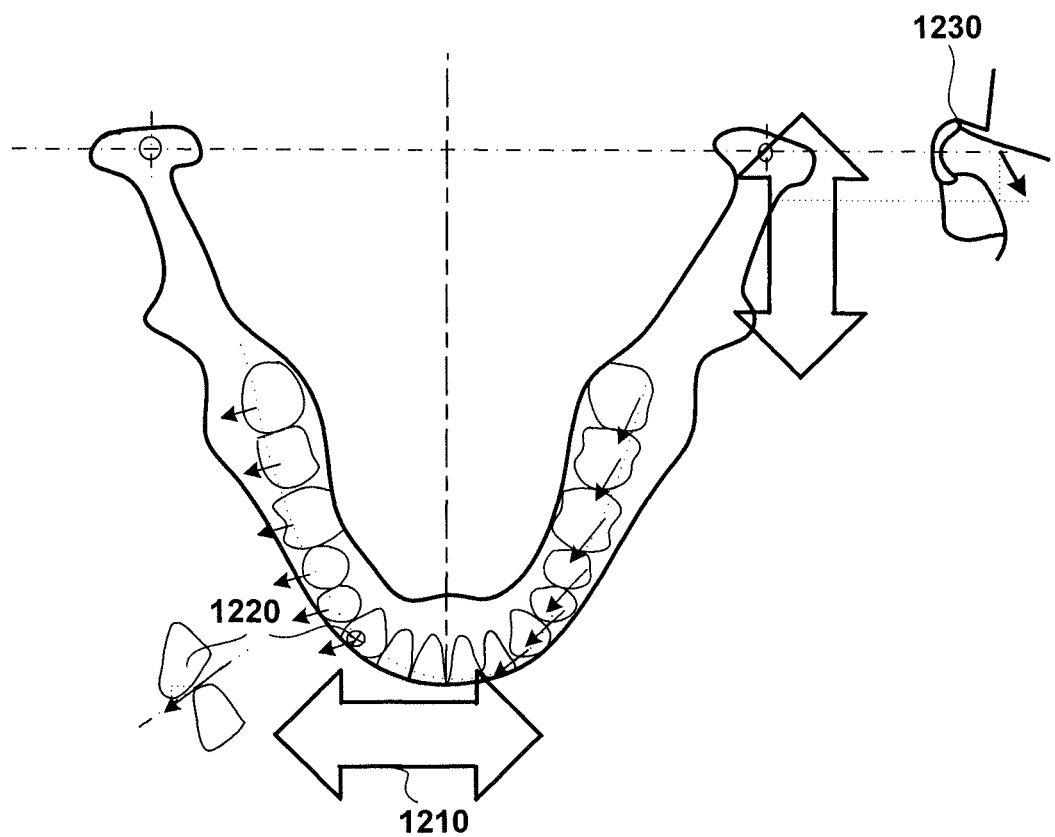
FIG. 12 illustrates an exemplary balanced occlusion motion envelope defined in laterotrusion.

In one example embodiment, said machining is in accordance with a three-dimensional file of the patient's anatomy. For example, in one example embodiment, a layered denture 200 may be manufactured with consideration for balanced occlusion of the layered denture when used by a denture user. In one embodiment, artificial dentition structure 220 is electronically defined by computer modeling wherein each layer is designed by defining the motion envelope of the user's mandible and each layer is shaped to accommodate that motion while remaining in contact through much or all of the motion. In one example embodiment, each layer may be defined by prismatic or other geometry. Furthermore, with reference to FIGS. 11 and 12, in one example embodiment, the motion envelope may be defined in protrusion 1110 from centric relation (mandible fully retracted) to protrusion where the central incisors are edge-to-edge. In one example embodiment, the motion envelope may be defined in laterotrusion 1210 where the buccal cusps of the posterior teeth are vertically aligned. Among other possible constraints, the mandible motion may be constrained in protrusion by incisal guidance 1120 and condylar shape 1130 and in laterotrusion by canine guidance 1220 and condylar shape 1230.

Figure 13:
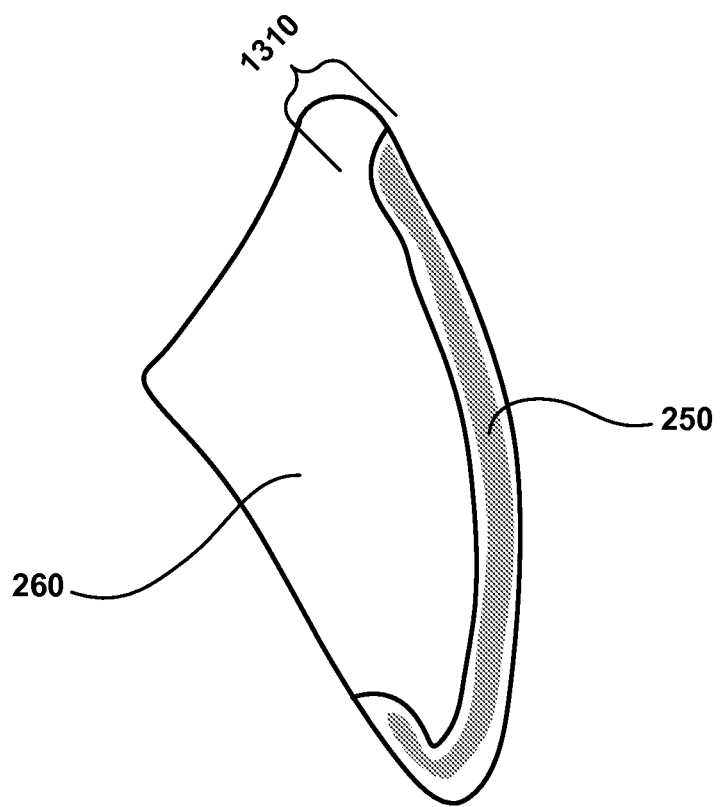
FIG. 13 illustrate illustrates a cut-away view of an exemplary artificial dentition structure.

With reference to FIGS. 2 and 14, in one example embodiment, the shape of artificial dentition structures 1410 is defined for the mandible motion envelope and the thickness and shape of dentin portion 260 of an artificial dentition structure 220 is offset (See FIG. 13; 1310) to provide sufficient spacing for balanced occlusion to be achieved upon the formation of enamel layer 250. Thus, both dentin portion 260 and enamel layer 250 of an artificial dentition structure 220 may be electronically defined and may be built based on digital images of the patient's anatomy which takes account of the mandible motion envelope and the offsets to achieve balanced occlusion. In one example embodiment, no grinding on the occlusal surface (See FIG. 11; 1140) of the enamel layer 250 will be required, due, for example, to this offsetting (See FIG. 13, 1310). In one example embodiment, this may result in a more aesthetically pleasing layered denture wherein the denture does not exhibit localized weakening due to grinding away of material. In one example embodiment, additional tooth morphology 1420 may be added, for example, for aesthetic purposes or for any other purpose.

An exemplary manufacturing process may proceed by iterative steps of machining pockets, then filling the machined pockets with a material, then machining the filled material to create a layer. In other exemplary manufacturing processes, multiple steps of machining and filling may occur in parallel, for example, at different locations or surfaces of the layered denture. In some example embodiments, at least one of dentin portion 260 and enamel layer 250 may be formed by machining or by 3D printing. In some example embodiments, additional material, for example, bonding material, is filled over a layer and machined, although any manufacturing process causing adhesion or bonding between layers may be utilized. In some embodiments, a layered denture may comprise multiple layers, although any number of layers suitable to form the denture as desired may be implemented.

The process for manufacturing layered dentures may be implemented by an apparatus as describing below. Moreover, it is to be expressly understood that any other systems or apparatus may also implement the process of the present invention.

In one instance, a fixture for holding the layered denture during manufacturing may be located adjacent to a material removing device. In some instances, the material removing device is a CNC or a CAD/CAM mill, although the material removing device can be a mill, grinder, laser cutter, or any other suitable device for forming the structures of the layered denture. In some instances, the material removing device and the fixture are movable relative to one another. In some instances, adjacent to the fixture may be at least one material delivery device to deliver raw material for the filling process described herein. Now, having discussed manufacturing of the reinforcement aspects, a layered denture may be further improved by adding a simulated root structure.

Figure 7:
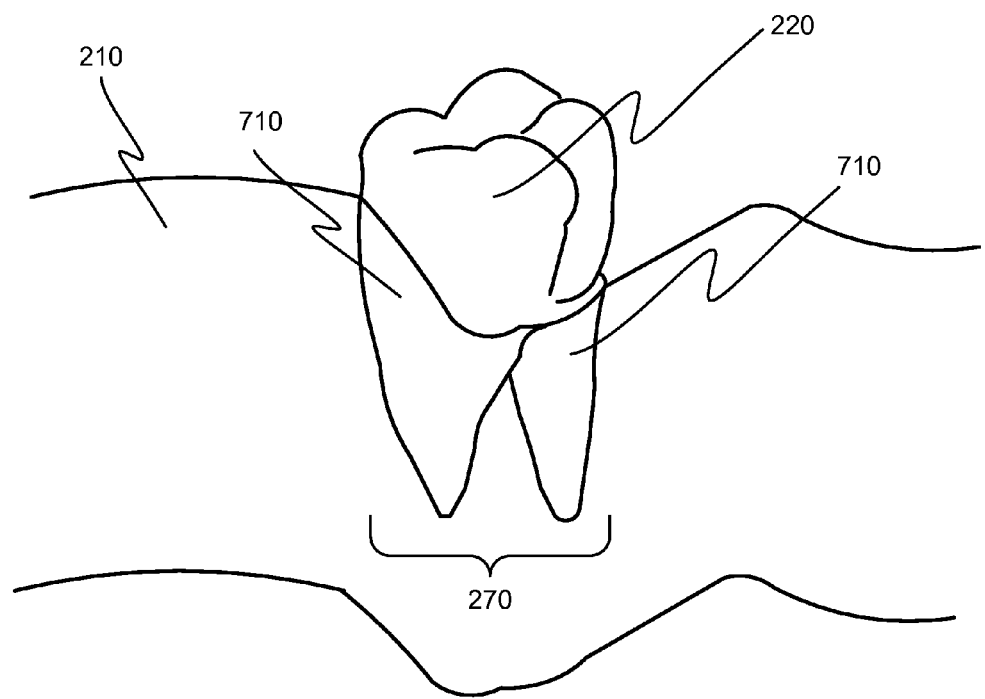
FIG. 7 is a view of an example embodiment of a layered denture having a root approximating structure that simulates anatomical roots.

With reference to FIG. 7, in accordance with one example embodiment, and the principles described herein, a layered denture 200 may comprise a base 210 having a first pocket 270 wherein said first pocket is configured to resemble a root of a tooth wherein a simulated root material 710 may be filled into a said first pocket 270.

Figure 16:
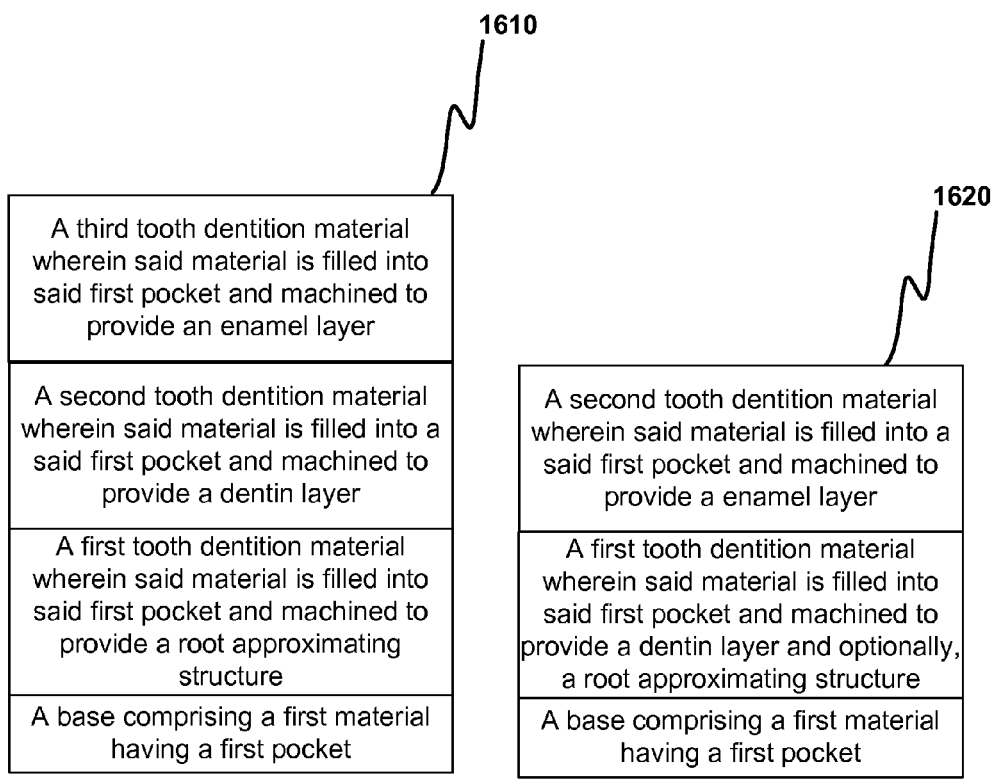
FIG. 16 illustrates functional relationships according to two example embodiments of an artificial dentition structure.

In some example embodiments, said simulated root material 710 provides a surface upon which artificial dentition structure 220 may be mounted. In other example embodiments, said simulated root material is machined to form part of a dentin portion 260 of an artificial dentition structure 220. For example, in some example embodiments (FIG. 16; 1620), said simulated root material 710 may be said earlier described first tooth dentition material filled in to the first pocket of base 200 and machined to provide a dentin layer 260. For example, an artificial dentition structure may comprise a first tooth dentition material wherein said material is filled into said first pocket and machined to provide at least one of a dentin layer and a root approximating structure and a second tooth dentition material wherein said material is filled into said first pocket and machined to provide an enamel layer.

Figure 15:
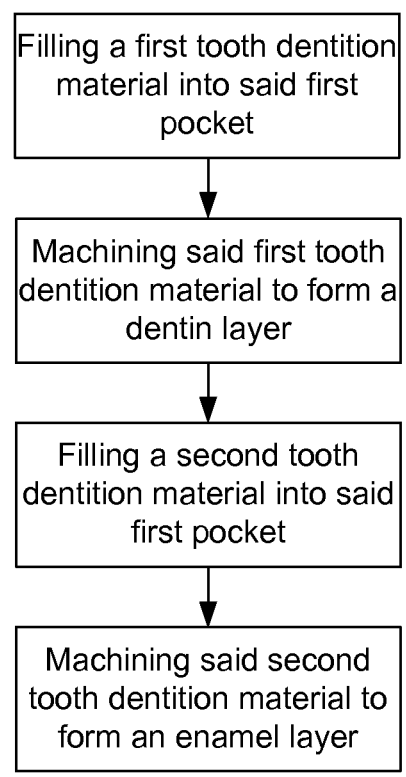
FIG. 15 is a flow chart illustrating an exemplary method of manufacturing a layered denture.

In some example embodiments (FIG. 15; 1610), said simulated root material 710 is a different material than said first tooth dentition material. For example, an artificial dentition structure may comprise a first tooth dentition material wherein said material is filled into said first pocket and machined to provide a root approximating structure; a second tooth dentition material wherein said material is filled into a said first pocket, and machined to provide a dentin layer; and a third tooth dentition material wherein said material is filled into said first pocket and machined to provide an enamel layer. Furthermore, an artificial dentition structure may in some example embodiments comprise any number of layers, including for instance, a single layer.

Figure 8:
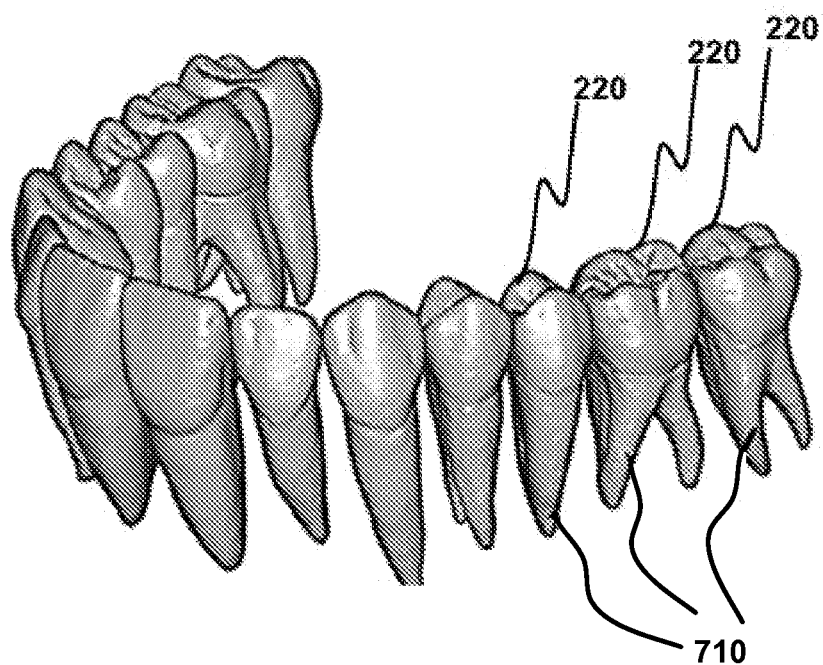
FIG. 8 is a cut away view of an example embodiment of a layered denture illustrating a root approximating structure that simulates anatomical roots.

With reference to FIG. 8, in one example embodiment, a plurality of artificial dentition structures 220 are illustrated in conjunction with simulated root material 710, but with base 210 cut away.

Figure 9:
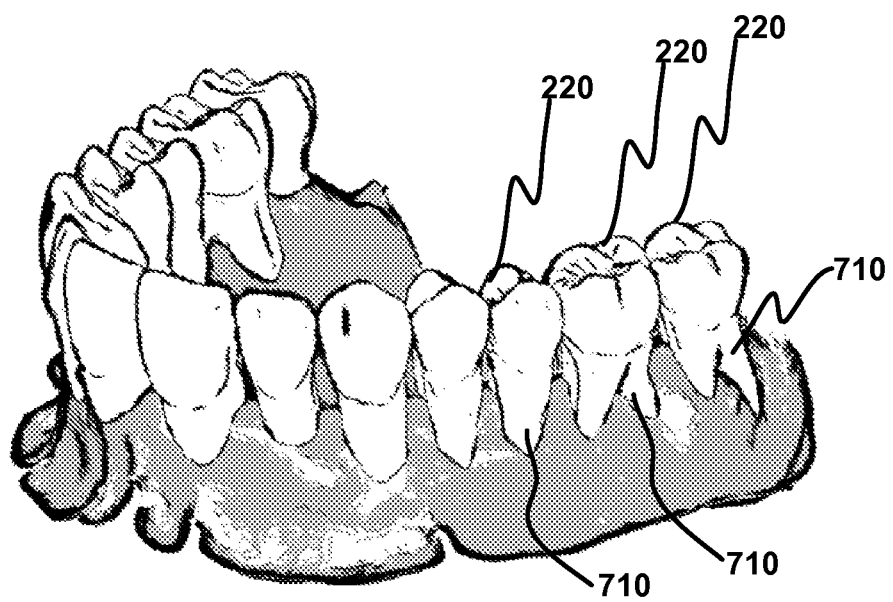
FIG. 9 is a cut away view of an example embodiment of a layered denture illustrating a root approximating structure that simulates anatomical roots and illustrating a denture base, with a portion of the denture base removed.

With reference to FIG. 9, in one example embodiment, a plurality of artificial dentition structures 220 are illustrated in conjunction with simulated root material 710, but with base 210 only partially cut away.

Figure 10:
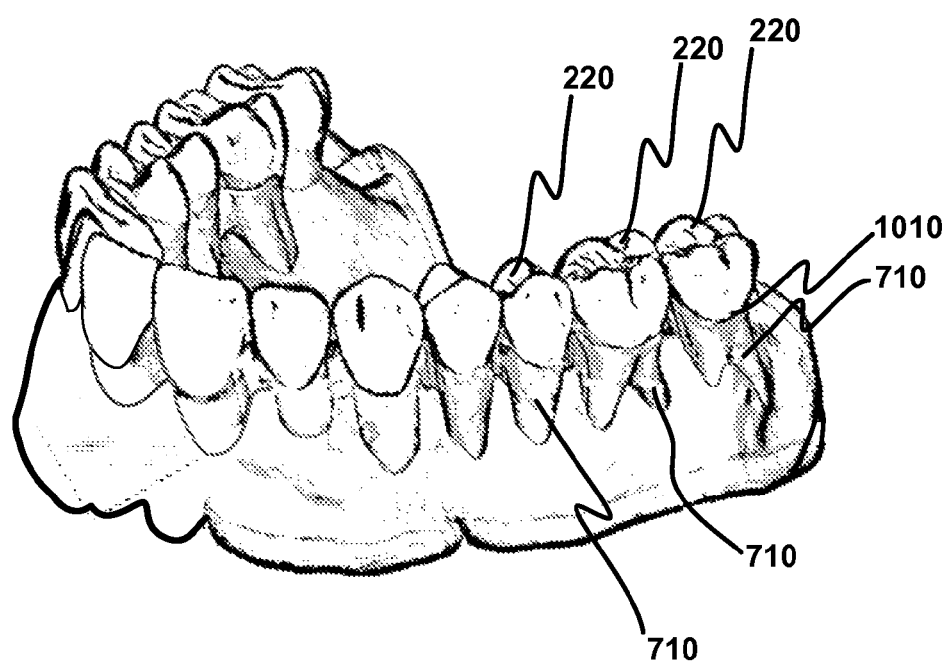
FIG. 10 is a cut away view of an example embodiment of a layered denture illustrating a root approximating structure that simulates anatomical roots and illustrating a denture base.

Furthermore, with reference to FIG. 10, a plurality of artificial dentition structures 220 are illustrated in conjunction with simulated root material 710, but with base 210 shaded so as to appear partially transparent. It can be recognized that in this exemplary embodiment, simulated root material 710 extends well below the gum lime 1010.

In addition, it should be noted that exemplary embodiments of a layered denture may include one of a simulated root structure, a support layer and a consideration for balanced occlusion, or any combination of such features. For example, a layered denture may include a support layer with balance occlusion (and without simulated root structure), a support layer with a simulated root structure (without balanced occlusion), a simulated root structure with balanced occlusion (without a support layer, and/or with a convention metal band configuration) or any other arrangement of such features individually or in combination. For purposes of describing the present invention, machining is used to describe the process of removing material from a part. This term, for purposes of the present invention includes but is not limited to milling, 3D printing, grinding, water jetting, laser cutting, electric discharge machining, CNC machining, ultrasonic machining, and any other type of mechanical, chemical, electrical, or other process suitable to conform filled material into to a layer.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "proximate," "proximately," or any other variation thereof, are intended to cover a physical connection, an electrical connection, a magnetic connection, an optical connection, a communicative connection, a functional connection, and/or any other connection. When language similar to "at least one of A, B, or C" is used, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A layered denture that is customized to a motion envelope defined by a patient's mandible, the denture comprising:
    a base comprising a first material having a first pocket;
    an artificial dentition structure in said first pocket, the said first pocket having a form to support said artificial dentition structure, the artificial dentition structure comprising:
        a first tooth dentition material in said first pocket and comprising a dentin layer; and
        a second tooth dentition material in said first pocket and comprising an enamel layer,
    wherein the defined motion envelope is in accordance with a three-dimensional file of the patient's anatomy comprising:
        a defined motion envelope of the user's mandible;
        an electronically modeled dentin layer modeled in a computing system according to the motion envelope and offset according to the motion envelope to provide sufficient spacing to achieve balanced occlusion; and
        an electronically modeled enamel layer modeled according to the motion envelope.

2. The denture in claim 1 comprising a third tooth dentition material in said first pocket and comprising a root approximating structure supported by the first pocket of the base.

3. The layered denture in claim 1 further comprising a first material wherein said first material may be filled into a second pocket and machined to provide a support layer;
    and a second material wherein said second material may be filled into said second pocket into a remaining cavity realized after machining of said support layer, said second material further machined to form a covering layer.

4. The layered denture according to claim 3 wherein said covering layer conforms to the geometry of a wearer's natural dentition.

5. A layered denture according to claim 1 wherein said base comprises a hardened polymethyl methacrylate (PMMA) material.

6. The layered denture in claim 1, wherein the first pocket resembles a root of a tooth.

* * * * *